United States Patent
Kwon et al.

(10) Patent No.: US 11,481,867 B2
(45) Date of Patent: Oct. 25, 2022

(54) DEVICE AND METHOD FOR REGISTERING THREE-DIMENSIONAL DATA

(71) Applicants: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

(72) Inventors: Ki Hoon Kwon, Daegu (KR); Seung Hyun Lee, Seoul (KR); Min Young Kim, Daegu (KR)

(73) Assignee: KOH YOUNG TECHNOLOGY INC., Daegu (KR)

(*) Notice: Subject to any disclaimer, the term of this patent is extended or adjusted under 35 U.S.C. 154(b) by 681 days.

(21) Appl. No.: 16/324,886

(22) PCT Filed: Aug. 9, 2017

(86) PCT No.: PCT/KR2017/008609
§ 371 (c)(1),
(2) Date: Feb. 11, 2019

(87) PCT Pub. No.: WO2018/030781
PCT Pub. Date: Feb. 15, 2018

(65) Prior Publication Data
US 2021/0287331 A1    Sep. 16, 2021

(30) Foreign Application Priority Data
Aug. 10, 2016  (KR) .................. 10-2016-0102070

(51) Int. Cl.
*G06T 3/00*     (2006.01)
*G06T 7/73*     (2017.01)

(52) U.S. Cl.
CPC .......... *G06T 3/0068* (2013.01); *G06T 3/0031* (2013.01); *G06T 7/75* (2017.01);
(Continued)

(58) Field of Classification Search
CPC combination set(s) only.
See application file for complete search history.

(56) References Cited

U.S. PATENT DOCUMENTS

| 5,531,520 A | 7/1996 | Grimson et al. |
| 5,999,840 A | 12/1999 | Grimson et al. |

(Continued)

FOREIGN PATENT DOCUMENTS

| CN | 104318552 | 1/2015 |
| CN | 105225219 | 1/2016 |

(Continued)

OTHER PUBLICATIONS

Anand A. Joshi et al., "Surface-Contrained Volumetric Brain Registration Using Harmonic Mappings", IEEE Transactions on Medical Imaging, Dec. 2007, vol. 26, No. 12., pp. 1657-1669.
(Continued)

*Primary Examiner* — Zhiyu Lu
(74) *Attorney, Agent, or Firm* — Kile Park Reed & Houtteman PLLC

(57) ABSTRACT

A method and a device for registering three-dimensional data are disclosed. The method for registering three-dimensional data comprises: generating first two-dimensional data by two-dimensionally converting first three-dimensional data indicating a surface of a three-dimensional model of a target, generating second two-dimensional data by two-dimensionally converting second three-dimensional data indicating at least a part of the three-dimensional surface of the target; determining a first matching region in the first two-dimensional data and a second matching region in the
(Continued)

second two-dimensional data by matching the second two-dimensional data to the first two-dimensional data; setting, as initial position, a plurality of points of the first three-dimensional data, which correspond to the first matching region and a plurality of points of the second three-dimensional data, which correspond to the second matching region; and registering the first three-dimensional data and the second three-dimensional data using the initial position.

17 Claims, 13 Drawing Sheets

(52) U.S. Cl.
CPC ............... *G06T 2207/10081* (2013.01); *G06T 2207/10088* (2013.01)

(56) References Cited

U.S. PATENT DOCUMENTS

| | | | |
|---|---|---|---|
| 6,904,163 B1 | 6/2005 | Fujimura et al. | |
| 2006/0013505 A1 | 1/2006 | Yau et al. | |
| 2006/0293557 A1 | 12/2006 | Chuanggui et al. | |
| 2007/0018975 A1 | 1/2007 | Chuanggui et al. | |
| 2008/0240574 A1 | 10/2008 | Weon Geun et al. | |
| 2013/0345491 A1 | 12/2013 | Saitoh et al. | |
| 2016/0364853 A1* | 12/2016 | Yamaguchi | G06V 20/20 |
| 2017/0124702 A1 | 5/2017 | Li et al. | |
| 2018/0101719 A1* | 4/2018 | Schickel | G06T 17/20 |
| 2018/0168532 A1* | 6/2018 | Nempont | A61B 6/12 |

FOREIGN PATENT DOCUMENTS

| | | |
|---|---|---|
| CN | 105261052 | 1/2016 |
| CN | 105654029 | 6/2016 |
| EP | 3 195 823 | 7/2017 |
| JP | 2950340 | 7/1999 |
| JP | 2001-78996 | 3/2001 |
| JP | 2006-518886 | 8/2006 |
| JP | 2009-501609 | 1/2009 |
| JP | 2011-180786 | 9/2011 |
| KR | 10-2008-0088778 | 10/2008 |
| KR | 10-2016-0034104 | 3/2016 |
| WO | 2012/121341 | 9/2012 |

OTHER PUBLICATIONS

Written Opinion for International Application No. PCT/KR2017/008609 with English translation, dated Nov. 8, 2017.
Takeshi Masuda, "Multiple Range Image Registration by Matching Local Log-Polar Range Images", vol. 47, No. SIG 10(CVIM 15), Jul. 2006.
Japanese Office Action, with English translation, corresponding to Japanese Application No. 2019-507783, dated Feb. 25, 2020.
International Search Report for International Application No. PCT/KR2017/008609; dated Nov. 8, 2017.
Laeyong Park et al.; "Rapid Rigid Registration Method Between Intra-Operative 2D XA and Pre-operative 3D CTA Images"; Journal of Korea Multimedia Society, vol. 16, No. 12, Dec. 2013, pp. 1454-1464.
Bastian Rieck et al.; "Unwrapping Highly-Detailed 3D Meshes of Rotationally Symmetric Man-Made Objects"; ISPRS Annals of the Photogrammetry, Remote Sensing and Spatial Information Sciences, vol. II-5/W1, 2013 XXIV International CIPA Symposium, Sep. 2-6, 2013, pp. 259-264.
Korean Office Action for Korean Application No. 10-2016-0102070 with English translation, dated Mar. 24, 2017.
Extended European Search Report corresponding to European Application No./Patent No. 17839799.8, dated Jul. 24, 2019.
Chinese Office Action corresponding to Chinese Application or Patent No. 2017800493782, dated Sep. 7, 2022.

* cited by examiner

800

1000

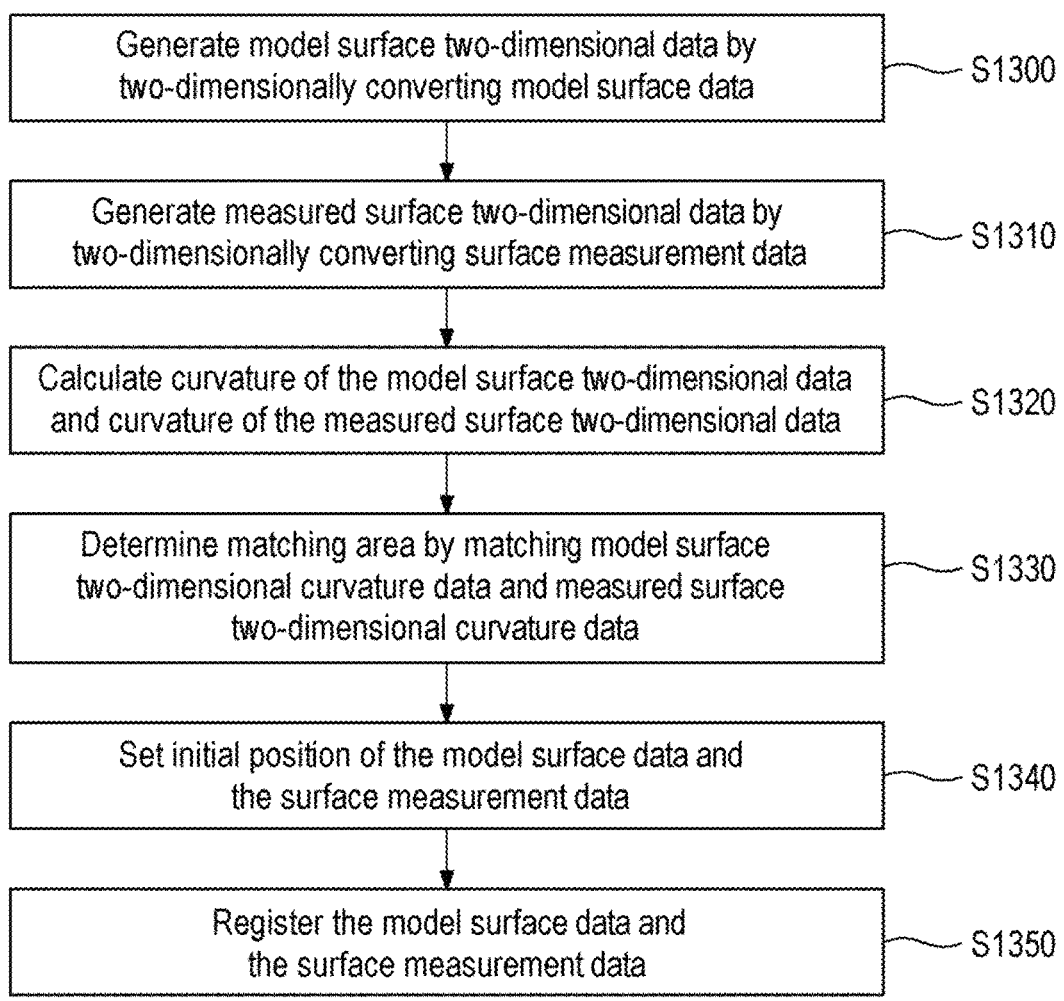

DEVICE AND METHOD FOR REGISTERING THREE-DIMENSIONAL DATA

TECHNICAL FIELD

The present disclosure relates to an apparatus and a method for registering three-dimensional data.

BACKGROUND

For the purpose of diagnosis and treatment in the medical field, a plurality of three-dimensional data may be acquired by different devices with regard to a target such as a patient's affected part. Each of the plurality of three-dimensional data may have a coordinate system unique to the device that has generated the corresponding data. For example, MRI data generated by modeling a patient's affected part using an MRI device and three-dimensional measurement data generated by imaging the corresponding affected part using a three-dimensional measurement device have different coordinate systems.

When a plurality of three-dimensional data having different coordinate systems are used together for the purpose of diagnosis or treatment, such three-dimensional data may be combined in an appropriate method. For example, when a surgeon operates a patient, for accurately recognizing the structure and shape of the patient's affected part and the outer part surrounding the affected part, MRI data generated by modeling the affected part in advance and three-dimensional measurement data generated by imaging the outer part of the affected part may be used together. In order to combine and use data having different coordinate systems, the coordinate systems related to the data need to be converted or aligned into a single coordinate system. For example, the coordinate system of the MRI data may be converted into the coordinate system of the three-dimensional measurement data, the coordinate system of the three-dimensional measurement data may be converted into the coordinate system of the MRI data, or the coordinate systems of the MRI data and three-dimensional measurement data may be converted into a third coordinate system.

Meanwhile, various registration algorithms are used for registration between data having different coordinate systems. According to an exemplary registration algorithm, the relative position between data may be changed in such a direction that the similarity between the data increases, and the relative position between data having the maximum similarity may be determined. Such a registration algorithm may designate an initial position in connection with data for the purpose of registration. If the initial position is erroneously designated with regard to data to be registered, the similarity between the registered data may not become maximum throughout the entire area of the data, although the similarity between the registered data may become locally maximum in the periphery of the initial position. In other words, if the initial position is erroneously designated with regard to data to be registered, inaccurate registration may be made between the data. There is another problem in that, if the initial position is erroneously designated with regard to the data to be registered in this manner, a long time is necessary to reach the optimal registration.

SUMMARY

The present disclosure provides a method and a device for registering three-dimensional data, the accuracy and efficiency of data registration may be improved by setting an initial position for registration on three-dimensional data based on two-dimensional data, which has been converted into three-dimensional data.

In accordance with an aspect of the present disclosure, there is provided a method for registering three-dimensional data. The method according to an exemplary embodiment comprises the steps of: generating first two-dimensional data by two-dimensionally converting first three-dimensional data indicating a surface of a three-dimensional model of a target; generating second two-dimensional data by two-dimensionally converting second three-dimensional data indicating at least a part of the three-dimensional surface of the target; determining a first matching area in the first two-dimensional data and a second matching area in the second two-dimensional data, respectively, by matching the second two-dimensional data to the first two-dimensional data; setting, as an initial position, a plurality of points of the first three-dimensional data, which correspond to the first matching area and a plurality of points of the second three-dimensional data, which correspond to the second matching area; and registering the first three-dimensional data and the second three-dimensional data using the initial position.

In addition, according to an exemplary embodiment, the determining the first matching area and the second matching area, respectively, includes: generating first two-dimensional curvature data and second two-dimensional curvature data by partially differentiating the first two-dimensional data and the second two-dimensional data, respectively; and determining the first matching area in the first two-dimensional curvature data and the second matching area in the second two-dimensional curvature data, respectively, by matching the first two-dimensional curvature data and the second two-dimensional curvature data.

According to at least one embodiment of the present disclosure, in order to designate an initial position for registration of three-dimensional data, matching between two-dimensional data, which have been converted from three-dimensional data, is performed instead of direct matching between the three-dimensional data to be registered. Data of an area matched in this manner is again converted three-dimensionally, thereby setting the initial position for registration. Consequently, an appropriate initial position may be set such that the accuracy and efficiency of registration between the three-dimensional data may be advantageously improved.

In addition, according to at least one embodiment of the present disclosure, in connection with matching two-dimensional data, which have been converted from three-dimensional data, matching between curvature data generated by partially differentiating the two-dimensional data is performed. Consequently, the initial position may be set more accurately such that the accuracy and efficiency of registration between the three-dimensional data may be advantageously improved further.

BRIEF DESCRIPTION OF DRAWINGS

FIG. 13 is a flowchart of a method for registering three-dimensional data according to an embodiment of the present disclosure.

DETAILED DESCRIPTION

Figure 1:
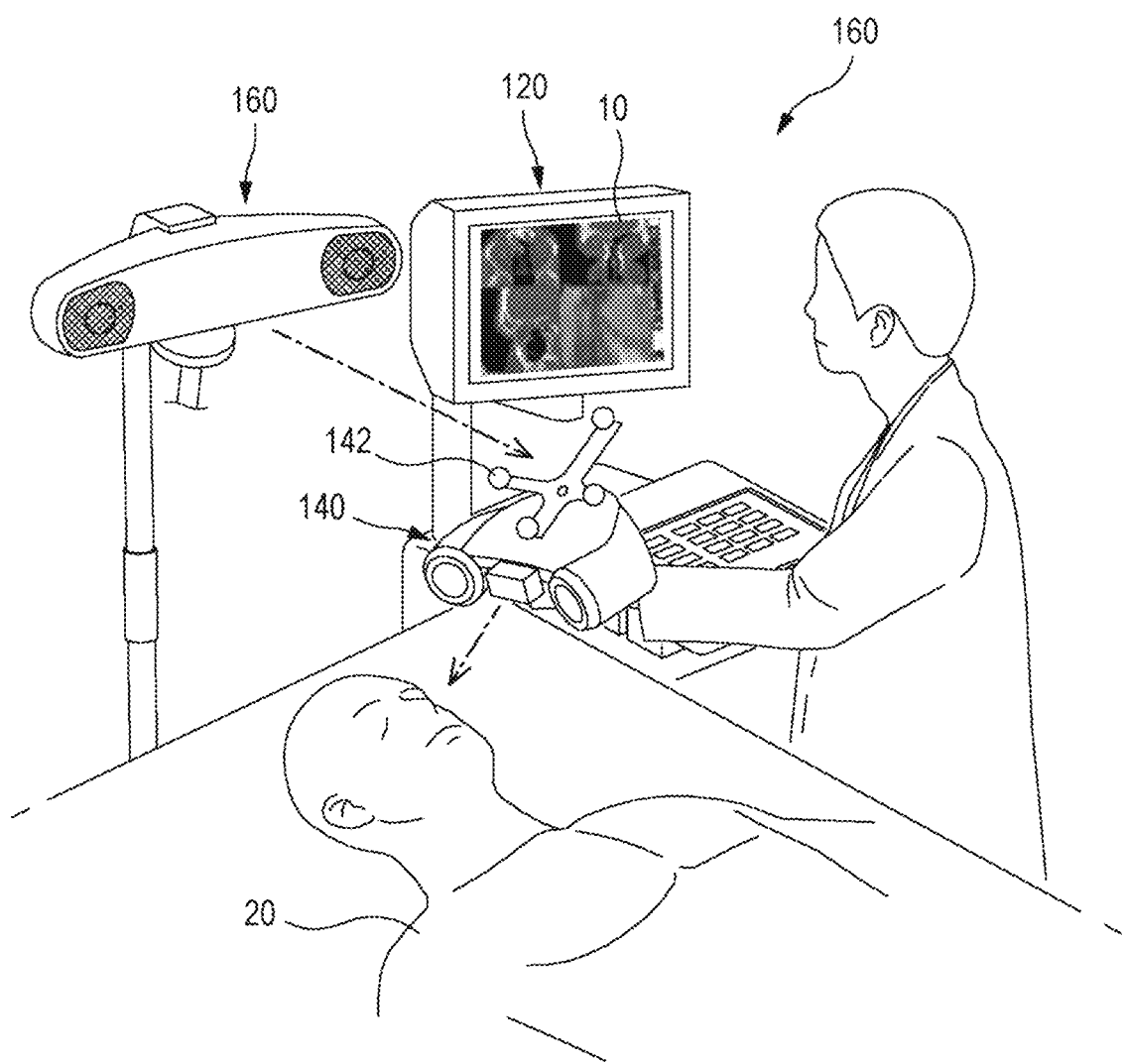
FIG. 1 schematically illustrates a surface registration system according to an embodiment of the present disclosure.

Exemplary embodiments of the present disclosure are provided for the purpose of describing the present disclosure. The embodiments of the present disclosure can be implemented in various forms, and the present disclosure is not to be interpreted as being limited by the following embodiments or detailed descriptions of the embodiments.

The term "unit" used in this specification refers to a software or hardware element such as an FPGA (field-programmable gate array) or an ASIC (application specific integrated circuit). However, the term "unit" is not limited to hardware and software. The "unit" may be configured to be stored in an addressable storage medium or may be configured to be able to reproduce one or more processors. For example, the "unit" includes, for example, elements such as software elements, object-oriented software elements, class elements, and task elements; a processor; a function; an attribute; a procedure; a subroutine; a program code segment; a driver; firmware; a microcode; a circuit; data; a database; a data structure; a table; an array; and a parameter. Functions provided inside elements and "units" may be combined with a smaller number of elements and "units" or may be further separated into additional elements and "units".

All technical terms and scientific terms used in this specification have meanings generally understood by a person skilled in the art to which the present disclosure pertains, unless otherwise defined. All terms used in this specification are selected for the purpose of clearly describing the present disclosure, not for the purpose of limiting the scope of the present disclosure.

A singular-form expression used in this specification may also include a plural-form expression unless otherwise specified, and the same applies to singular-form expressions used in the claims.

Expressions such as "first" and "second" used in various embodiments of the present disclosure are for the purpose of identifying a plurality of elements from one another, not for the purpose of limiting the order or importance of the corresponding elements.

Expressions such as "include" and "have" used in this specification are to be understood as open-ended terms incorporating the possibility that the same will include other embodiments, unless otherwise specified in the phrase or sentence including the corresponding expression.

As used in this specification, the expression "based on" denotes at least one factor that affects the behavior or operation of decision or determination described in the phrase including the expression, and does not exclude an additional factor that affects the behavior or operation of decision or determination.

It is to be understood that, when a specific element is described as being "connected" or "joined" to another element in this specification, the specific element may be directly connected or joined to the other element, but another new element may also exist between the specific element and the other element.

Hereinafter, embodiments of the present disclosure will be described in detail with reference to the accompanying drawings. The same elements in the drawings are given the same reference numerals, and repeated descriptions of the same elements will be omitted.

FIG. 1 schematically illustrates a surface registration system 100 according to an embodiment of the present disclosure. As illustrated in FIG. 1, the surface registration system 100 includes a three-dimensional data registration device 120, a three-dimensional scanner 140, and an optical tracker 160.

The three-dimensional data registration device 120 according to the present embodiment may store and display model data generated by modeling a target such as an affected part of a patient 20. As used herein, the "model data" may refer to three-dimensional data of a target generated by a modeling device (not illustrated), such as a CT device or an MRI device, that models the three-dimensional shape or structure of the target. The model data may have a unique coordinate system (for example, $x_1y_1z_1$ coordinate system) related to the modeling device. In the example illustrated in FIG. 1, the model data may be CT/MRI data 10 generated by a modeling device, such as a CT device or an MRI device, modeling a part of the body of the patient 20 as a target. In this case, the CT/MRI data 10 have a unique coordinate system related to the CT/MRI device.

The three-dimensional scanner 140 may generate measured surface data by measuring a surface of a target three-dimensionally by using various techniques, including photogrammetry, structured light 3D scanning, modulated light 3D scanning, stereo photography, LIDAR, ultrasonic TOF (Time-of-Flight), or laser TOF. As illustrated in FIG. 1, the three-dimensional scanner 140 may generate measured surface data by measuring at least a part of a surface of the body of a patient 20 as a target. The target measured by the three-dimensional scanner 140 may be the outer surface of the target modeled as model data described above, or a part thereof. For example, when the model data is data obtained by modeling a three-dimensional shape of a head of the patient 20, the measured surface data may be data obtained by measuring outer shapes, such as the eyes, nose, mouth, and ears, on the surface of the head of the patient 20. The measured surface data may have a unique coordinate system (for example, $x_2y_2z_2$ coordinate system) related to the three-dimensional scanner 140. The coordinate system of the measured surface data may differ from the coordinate system (for example, $x_1y_1z_1$ coordinate system) of the model data and may also differ from the coordinate system (for example, $x_0y_0z_0$ coordinate system) of the optical tracker 160.

The surface registration system 100 according to an embodiment of the present disclosure may convert or align the coordinate system (for example, $x_1y_1z_1$ coordinate system) of model data and the coordinate system (for example, $x_2y_2z_2$ coordinate system) of measured surface data into the coordinate system (for example, $x_0y_0z_0$ coordinate system) of the optical tracker 160. The three-dimensional data registration device 120 may perform registration of model data and measured surface data, which have different coordinate systems. In order to perform registration of the model data and the measured surface data, the three-dimensional data registration device 120 may extract surface data (hereinafter, referred to as "model surface data") from the model data and may perform registration between the model surface data and the measured surface data. In this regard, the coordinate system of the model surface data may be identical to the coordinate system (for example, $x_1y_1z_1$ coordinate system) of the model data. In addition, the optical tracker 160 may convert the coordinate system (for example, $x_2y_2z_2$ coordinate system) of the measured surface data into the coordinate system (for example, $x_0y_0z_0$ coordinate system) of the optical tracker 160 via a marker 142 mounted on the three-dimensional scanner 140. Consequently, the coordinate system (for example, $x_1y_1z_1$ coordinate system) of the model data and the model surface data, which are registered with the measured surface data by the three-dimensional registration device 120, is also converted into the coordinate system (for example, $x_0y_0z_0$ coordinate system) of the optical tracker 160.

The three-dimensional data registration device 120 may perform registration between the model surface data and the measured surface data using various registration algorithms. For example, the three-dimensional data registration device 120 may perform registration using an ICP (Iterative Closest Point) algorithm. The three-dimensional data registration device 120 may set an initial position with regard to three-dimensional data for the purpose of registration, and may execute a registration algorithm based on the set initial position. For example, the three-dimensional data registration device 120 may calculate the similarity between the model surface data and the measured surface data based on a predetermined area or predetermined point in the model surface data and in the measured surface data as initial positions, and may change a relative position of the model surface data with regard to the measured surface data in such a direction that the similarity increases. For example, the three-dimensional data registration device 120 may define points in the model surface data and in the measured surface data, which are at the shortest distance, as corresponding point sets, and may calculate the similarity based on a sum of distances between the corresponding point sets.

In order to set the initial position used for registration, the three-dimensional data registration device 120 may use model surface two-dimensional data, into which model surface data is converted two-dimensionally, and measured surface two-dimensional data, into which measured surface data is converted two-dimensionally. The three-dimensional data registration device 120 may map the three-dimensional coordinates of respective points of the model surface data (or the measured surface data) to two-dimensional coordinates of each point of the model surface two-dimensional data (or the measured surface two-dimensional data) and values (for example, brightness values) of the corresponding points. According to an embodiment, the three-dimensional data registration device 120 may perform two-dimensional data conversion through spherical unwrapping. According to the spherical unwrapping, two-dimensional coordinates of each point of the two-dimensional data may be determined from two angle components of corresponding points in a three-dimensional spherical coordinate system. In addition, the value of each point of the two-dimensional data can be determined by the distance from a corresponding point in the three-dimensional spherical system to an origin. According to another embodiment, the three-dimensional data registration device 120 may use various two-dimensional data conversion algorithms such as cylindrical unwrapping conversion and equirectangular unwrapping.

According to an embodiment, the three-dimensional data registration device 120 may calculate the curvature of each of the model surface two-dimensional data and the measured surface two-dimensional data, thereby generating model surface two-dimensional curvature data and measured surface two-dimensional curvature data. According to an embodiment, the three-dimensional data registration device 120 may determine the value of each point of the model surface two-dimensional curvature data (or measured surface two-dimensional curvature data) from the difference between a value of a corresponding point and values of a plurality of adjacent points, in connection with the model surface two-dimensional data (or measured surface two-dimensional data). According to an embodiment, the three-dimensional data registration device 120 may generate two-dimensional curvature data by partially differentiating a value of the two-dimensional data.

The three-dimensional data registration device 120 may match the model surface two-dimensional data and the measured surface two-dimensional data, and may determine matching areas. Furthermore, in connection with model surface data and measured surface data, which are three-dimensional data, the three-dimensional data registration device 120 may set a surface area of the model surface data, which corresponds to the matching area of the model surface two-dimensional data, as the initial position for registration, and may set a surface area of the measured surface data, which corresponds to the matching area of the measured surface two-dimensional data, as the initial position for registration. According to an embodiment, the three-dimensional data registration device 120 may match the model surface two-dimensional curvature data and the measured surface two-dimensional curvature data, instead of matching the model surface two-dimensional data and the measured surface two-dimensional data, in order to determine matching areas. Setting initial positions of the model surface data and the measured surface data will be described in more detail with reference to FIG. 2 to FIG. 8.

Meanwhile, the optical tracker 160 may image the marker 142 mounted on the three-dimensional scanner 140, thereby generating a marker image. The optical tracker 160 may analyze the size and position of the marker 144 appearing on the marker image, thereby determining the position and posture of the three-dimensional scanner 140, and may accordingly establish a conversion relationship between the coordinate system related to the three-dimensional scanner 140 and the coordinate system related to the optical tracker 160.

Since the measured surface data on the coordinate system related to the three-dimensional scanner 140 is registered to the model surface data on the coordinate system for the model data as described above, the optical tracker 160 may establish a conversion relationship between the coordinate system of the model data and the coordinate system related to the three-dimensional scanner 140. By using the conversion relationship between the coordinate system related to the three-dimensional scanner 140 and the coordinate system related to the optical tracker 160 and the conversion relationship between the coordinate system of the model data and the coordinate system related to the three-dimensional scanner 140, the optical tracker 160 may acquire a conversion relationship between the coordinate system of the model data and the coordinate system related to the optical tracker 160, and may handle the model data within the coordinate system related to the optical tracker 160.

FIG. 1 illustrates a patient 20 as a target of model data and measured surface data, but the present disclosure is not limited thereto. The target according to the present disclosure may be, for example, any object having a three-dimensional shape, a human, or an animal.

Figure 2:
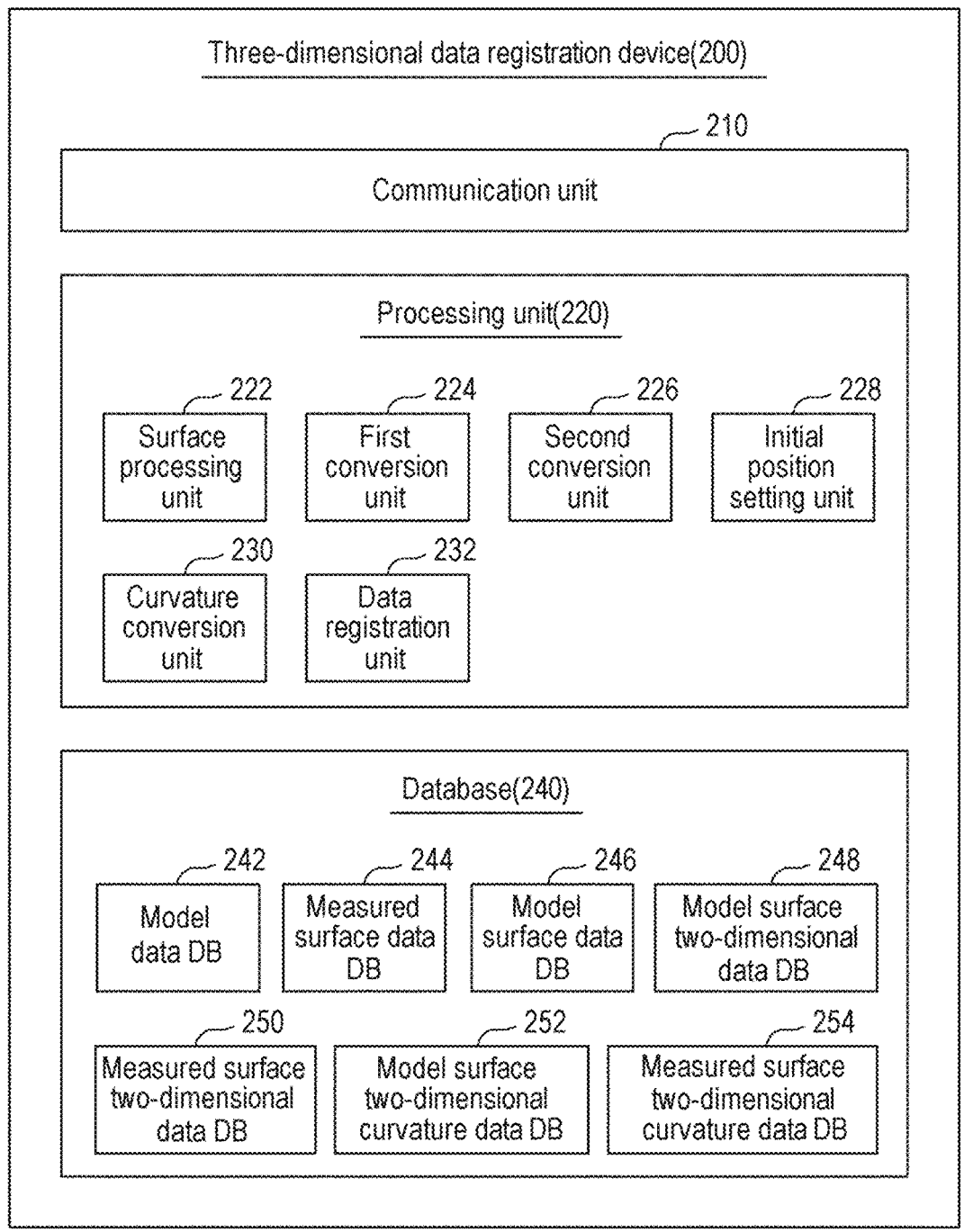
FIG. 2 is a block diagram illustrating the detailed configuration of a three-dimensional data registration device according to an embodiment of the present disclosure.

FIG. 2 is a block diagram illustrating the detailed configuration of a three-dimensional data registration device 200 according to an embodiment of the present disclosure. According to multiple embodiments, the three-dimensional data registration device 200 of FIG. 2 may include all technical features of the three-dimensional data registration device 120 of FIG. 1. As illustrated in FIG. 2, the three-dimensional data registration device 200 includes a communication unit 210, a processing unit 220, and a database 240.

The communication unit 210 may communicate with an external device, such as a modeling device (not illustrated) that generates model data, the three-dimensional scanner 140 of FIG. 1, and the optical tracker 160. Low-level elements of the communication unit 210, which are for communicating with such external devices, may be integrally configured as a single hardware device.

The processing unit 220 may process information related to three-dimensional data registration. The processing unit 220 includes a surface processing unit 222, a first conversion unit 224, a second conversion unit 226, an initial position setting unit 228, a curvature conversion unit 230, and a data registration unit 232. In addition, the database 240 may store data related to three-dimensional data registration. The database 240 may include a model data DB 242, a measured surface data DB 244, a model surface data DB 246, a model surface two-dimensional data DB 248, a measured surface two-dimensional data DB 250, a model surface two-dimensional curvature data DB 252, and a measured surface two-dimensional curvature data DB 254. FIG. 2 illustrates low-level elements that constitute the database 240 independently, but the present disclosure is not limited thereto. For example, at least some of the low-level elements of the database 240 may be integrally configured.

The model data DB 242 stores model data that indicates a three-dimensional model of the target. According to an embodiment, the model data may be CT/MRI data 10 generated by modeling the shape of the head of the patient 20 using the CT/MRI device. In this case, the model data may be received from the CT/MRI device through the communication unit 210 and may be stored in the model data DB 242.

The measured surface data DB 244 may store measured surface data that indicates at least a part of a three-dimensional surface of the target. According to an embodiment, the measured surface data may be data obtained by measuring outer shapes of the patient 20, such as the eyes, ears, and nose, by using the three-dimensional scanner 140 of FIG. 1. In this case, the measured surface data may be stored in the measured surface data DB 244 from the three-dimensional scanner 140 through the communication unit 210.

The surface processing unit 222 may extract model surface data from the model data stored in the model data DB 242. The model surface data indicates the surface of a three-dimensional model of the target, and may have the same coordinate system (for example, $x_1y_1z_1$ coordinate system) as that of the model data. For example, when the model data is CT/MRI data 10 indicating the three-dimensional shape of the head of the patient 20, the model surface data indicates the three-dimensional surface of the head of the patient 20. The surface processing unit 222 may store the model surface data in the model surface data DB 246.

The first conversion unit 224 may two-dimensionally convert the model surface data stored in the model surface data DB 246. The first conversion unit 224 may two-dimensionally convert the model surface data through unwrapping. As used herein, unwrapping may refer to a two-dimensional data conversion algorithm defined by, for example, the paper "Unwrapping highly-detailed 3D meshes of rotationally symmetric man-made objects (Rieck, Bastian, Hubert Mara, and Susanne Kromker; (2013): 259-264)". It is possible to use, as the unwrapping, spherical unwrapping, cylindrical unwrapping, or equirectangular unwrapping. The first conversion unit 224 may select the type of unwrapping based on the three-dimensional shape indicated by the model surface data. For example, when the model surface data is spherical as in the case of the head, the first conversion unit 224 may select the spherical unwrapping. As another example, when the model surface data is cylindrical as in the case of an arm or a leg, the first conversion unit 224 may select the cylindrical unwrapping.

When the spherical unwrapping is selected, the first conversion unit 224 may determine the center coordinate of the model surface data. According to an embodiment, the first conversion unit 224 may determine an average value of all points of the model surface data as the center coordinate. In addition, the first conversion unit 224 may parallel-move the model surface data such that the center coordinate of the model surface data becomes the origin of the coordinate system (for example, $x_1y_1z_1$ coordinate system). In addition, the first conversion unit 224 may calculate an average value of distances from the center coordinate to each point of the model surface data as the reference distance. Thereafter, the first conversion unit 224 may convert the three-dimensional coordinate system (for example, $x_1y_1z_1$ coordinate system) including x-axis, y-axis, and z-axis into a two-dimensional coordinate system (for example, $\phi_1\theta_1$ coordinate system) including $\phi$-axis and $\theta$-axis using equation 1 below, based on the calculated reference distance. Consequently, the first conversion unit 224 may obtain model surface two-dimensional data, which have been converted two-dimensionally from the model surface data.

$$r_i = \sqrt{x_i^2 + y_i^2 + z_i^2}$$
$$\phi_i = \arctan\left(\frac{y_i}{x_i}\right)$$
$$\theta_i = \arcsin\left(\frac{z_i}{r_i}\right)$$
[equation 1]

It is assumed in equation 1 that the model surface data is spherically unwrapped with reference to the y-axis. In this regard, $r_i$ refers to the distance from the center coordinate (for example, the origin of the three-dimensional coordinate system) to each point of the model surface data. According to an embodiment, the value (for example, brightness value) for each point of the model surface two-dimensional data may refer to the distance from a point of the model surface data, which corresponds to the corresponding point, to the center coordinate. For example, the larger the distance from a specific point of the model surface data to the center coordinate (in other words, the farther from the center coordinate), the larger the brightness value of the corresponding point of the model surface two-dimensional data may become. The first conversion unit 224 may store the model surface two-dimensional data, which have been converted from the model surface data, in the model surface two-dimensional data DB 248. The conversion into the model surface two-dimensional data will be described later with reference to FIG. 3.

The second conversion unit 226 may two-dimensionally convert measured surface data stored in the measured surface data DB 244. The second conversion unit 226 may two-dimensionally convert measured surface data through unwrapping. It is possible to use, as the unwrapping, spherical unwrapping, cylindrical unwrapping, or equirectangular unwrapping. The second conversion unit 226 may select the same type of unwrapping as that of unwrapping selected by the first conversion unit 224. For example, when model surface data is spherically unwrapped by the first conversion unit 224, the second conversion unit 226 may also spherically unwrap the measured surface data.

Even when model surface data that indicates the surface of the target has a spherical shape such as the head, measured surface data acquired by scanning a part of the surface of the target may not have a spherical shape, as in the case of eyes or ears. In order to spherically unwrap such non-spherical measured surface data, the second conversion unit 226 may use an unwrapping algorithm, for example, disclosed in the paper "Unwrapping highly-detailed 3D meshes of rotationally symmetric man-made objects (Rieck, Bastian, Hubert Mara, and Susanne Kromker; (2013): 259-264)". For example, the second conversion unit 226 may generate a virtual sphere having, as a radius, the reference distance used for two-dimensional conversion of model surface data by the first conversion unit 224 (for example, the average value of distances from the center coordinate to each point of the model surface data). The second conversion unit 226 may parallel-move or rotation-move the measured surface data such that the measured surface data exists on the surface of the virtual sphere. Thereafter, the second conversion unit 226 may convert the three-dimensional coordinate system (for example, $x_2 y_2 z_2$ coordinate system) including x-axis, y-axis, and z-axis into a two-dimensional coordinate system (for example, $\phi_2 \theta_2$ coordinate system) including $\phi$-axis and $\theta$-axis using the above-mentioned equation 1, based on the reference distance. Consequently, the second conversion unit 226 may obtain measured surface two-dimensional data, which have been converted two-dimensionally from the measured surface data.

According to an embodiment, the value (for example, brightness value) of each point of measured surface two-dimensional data may indicate the distance from a point of measured surface data, which corresponds to the corresponding point, to the center coordinate of a virtual sphere. For example, the larger the distance from a specific point of the measured surface data to the center coordinate of the virtual sphere (in other words, the farther from the center coordinate), the larger the brightness value of the corresponding point of the measured surface two-dimensional data may become. The second conversion unit 226 may store the measured surface two-dimensional data, which have been converted from the measured surface data, on the measured surface two-dimensional data DB 250. The conversion into the measured surface two-dimensional data will be described later with reference to FIG. 4 and FIG. 5.

The initial position setting unit 228 may match the model surface two-dimensional data stored in the model surface two-dimensional data DB 248 and the measured surface two-dimensional data stored in the measured surface two-dimensional data DB 250. According to an embodiment, the initial position setting unit 228 matches the model surface two-dimensional data and the measured surface two-dimensional data by using an NCC (Normalized Cross Correlation) algorithm. The initial position setting unit 228 may determine, in connection with the model surface two-dimensional data, an area having the maximum similarity to a specific area of the measured surface two-dimensional data, thereby matching the model surface two-dimensional data and the measured surface two-dimensional data, and may determine matching areas as areas of the model surface two-dimensional data and the measured surface two-dimensional data that are matched as described above. For example, the initial position setting unit 228 calculates the similarity between the model surface two-dimensional data and the measured surface two-dimensional data while continuously changing the position of a specific area of the measured surface two-dimensional data with regard to the model surface two-dimensional data by a predetermined distance. In addition, the initial position setting unit 228 determines matching areas as areas of the model surface two-dimensional data and the measured surface two-dimensional data, which have the maximum similarity.

According to embodiments, the initial position setting unit 228 may express the matching area determined from the model surface two-dimensional data as a plurality of points. For example, when the determined matching area is a rectangle, the initial position setting unit 228 may express such a rectangular area in terms of two facing vertices of the corresponding matching area or four vertices thereof. In addition, the initial position setting unit 228 may express a matching area of the measured surface two-dimensional data as a plurality of points. Each of a plurality of points specified by the initial position setting unit 228 may have a $\phi \theta$ coordinate system (for example, $\phi_1 \theta_1$ coordinate system and $\phi_2 \theta_2$ coordinate system). In addition, matching between the model surface two-dimensional data and the measured surface two-dimensional data will be described later with reference to FIG. 6 and FIG. 7.

The initial position setting unit 228 may set an area of the model surface data, which corresponds to the matching area determined from the model surface two-dimensional data, and an area of the measured surface data, which corresponds to the matching area determined from the measured surface two-dimensional data, as initial positions, respectively. For example, the initial position setting unit 228 may determine a plurality of coordinates, which correspond to coordinates of the matching area of the model surface two-dimensional data, within the model surface data, and may set an area defined by the plurality of determined coordinates as the initial position. In addition, the initial position setting unit 228 may determine a plurality of coordinates, which correspond to coordinates of the matching area of the measured surface two-dimensional data, within the measured surface data, and may set an area defined by the plurality of determined coordinates as the initial position.

In order to set the initial position of the model surface data, the initial position setting unit 228 may use the inverse conversion of the unwrapping that is used by the first conversion unit 224 during two-dimensional conversion. For example, when the first conversion unit 224 converts model surface data two-dimensionally through spherical unwrapping, the initial position setting unit 228 may set the initial position of the model surface data through the inverse conversion of the spherical unwrapping. In this case, the initial position setting unit 228 may perform three-dimensional conversion based on the reference distance that is used by the first conversion unit 224 during spherical unwrapping. The initial position related to the model surface data has a xyz coordinate system (for example, $x_1y_1z_1$ coordinate system).

In order to set the initial position of the measured surface data, the initial position setting unit 228 may use the inverse conversion of the unwrapping that is used by the second conversion unit 226 during two-dimensional conversion. For example, when the second conversion unit 226 converts measured surface data two-dimensionally through spherical unwrapping, the initial position setting unit 228 may set the initial position of the measured surface data through the inverse conversion of the spherical unwrapping. In this case, the initial position setting unit 228 may perform three-dimensional conversion based on the reference distance that is used by the second conversion unit 226 during spherical unwrapping. The initial position related to the model surface data has an xyz coordinate system (for example, $x_2y_2z_2$ coordinate system). Setting initial positions with regard to the model surface data and the measured surface data will be described later with reference to FIG. 11 and FIG. 12.

According to multiple embodiments, initial positions of the model surface data and the measured surface data may be set based on data obtained by partially differentiating the model surface two-dimensional data and data obtained by partially differentiating the measured surface two-dimensional data, respectively. To this end, the curvature conversion unit 230 may generate model surface two-dimensional curvature data and measured surface two-dimensional curvature data by partially differentiating the model surface two-dimensional data and the measured surface two-dimensional data, respectively. In this case, the initial position setting unit 228 may determine matching areas by matching the model surface two-dimensional curvature data and the measured surface two-dimensional curvature data.

The curvature conversion unit 230 may generate model surface two-dimensional curvature data based on the value of a corresponding point of the model surface two-dimensional data and the value of a plurality of adjacent points. According to an embodiment, the value (for example, brightness value) of each point of the model surface two-dimensional curvature data may indicate the difference between the value of the corresponding point of the model surface two-dimensional data and the average value of a plurality of adjacent points (for example, four, eight, or fourteen points). The model surface two-dimensional curvature data may be average curvature data that indicates the average curvature of the model surface two-dimensional data, or Gaussian curvature data that indicates the Gaussian curvature of the model surface two-dimensional data.

The curvature conversion unit 230 may generate measured surface two-dimensional curvature data based on the value of a corresponding point of the measured surface two-dimensional curvature data and the value of a plurality of adjacent points. According to an embodiment, the value (for example, brightness value) of each point of the measured surface two-dimensional curvature data may indicate the difference between the value of the corresponding point of the measured surface two-dimensional data and the average value of a plurality of adjacent points (for example, four, eight, or fourteen points). The measured surface two-dimensional curvature data may be average curvature data that denote the average curvature of the measured surface two-dimensional data, or Gaussian curvature data that indicates the Gaussian curvature of the measured surface two-dimensional data.

According to an embodiment, the curvature conversion unit 230 may generate average curvature data and Gaussian curvature data with regard to the model surface two-dimensional data, respectively, and may generate average curvature data and Gaussian curvature data with regard to the measured surface two-dimensional data, respectively. In this case, the initial position setting unit 228 may match the average curvature data related to the model surface two-dimensional data and the average curvature data related to the measured surface two-dimensional data, thereby identifying a first area of the model surface two-dimensional data, with which the measured surface two-dimensional data is matched. In addition, the initial position setting unit 228 may match the Gaussian curvature data related to the model surface two-dimensional data and the Gaussian curvature data related to the measured surface two-dimensional data, thereby identifying a second area of the model surface two-dimensional data, with which the measured surface two-dimensional data is matched. Thereafter, the initial position setting unit 228 may determine the intermediate value of the first area and the second area as a matching area, thereby setting the initial position.

According to an embodiment, the curvature conversion unit 230 performs partial differentiation by using a mask operation. For example, when a mask having the size of 3*3 is used, the curvature conversion unit 230 calculates the difference between a value of a predetermined point and a value of eight adjacent points, thereby calculating the curvature of the corresponding point. For example, the larger the curvature, the smaller the brightness value of the corresponding point that the curvature conversion unit 230 may indicate. The model surface two-dimensional curvature data and the measured surface two-dimensional curvature data, generated by the curvature conversion unit 230, may be stored in the model surface two-dimensional curvature data DB 252 and the measured surface two-dimensional curvature data DB 254, respectively. Conversion into the model surface two-dimensional curvature data and the measured surface two-dimensional curvature data will be described later with reference to FIG. 8 to FIG. 10.

According to at least one embodiment, the model surface two-dimensional curvature data and the measured surface two-dimensional curvature data generated by the curvature conversion unit 230 may indicate a change in the data value more clearly than the model surface two-dimensional data and the measured surface two-dimensional data. Accordingly, when the initial position for registration is set by matching the model surface two-dimensional curvature data and the measured surface two-dimensional curvature data, the registration between the data advantageously has improved accuracy and efficiency.

The data registration unit 232 may perform registration between model surface data and measured surface data based on the initial position set by the initial position setting unit 228. According to an embodiment, the data registration unit 232 may perform registration between the data using an ICP (Iterative Closest Point) algorithm. The model surface data and the measured surface data, which are registered, have the same coordinate system. For example, the measured surface data is aligned according to the coordinate system (for example, $x_1y_1z_1$ coordinate system) of the model surface data.

Figure 3:
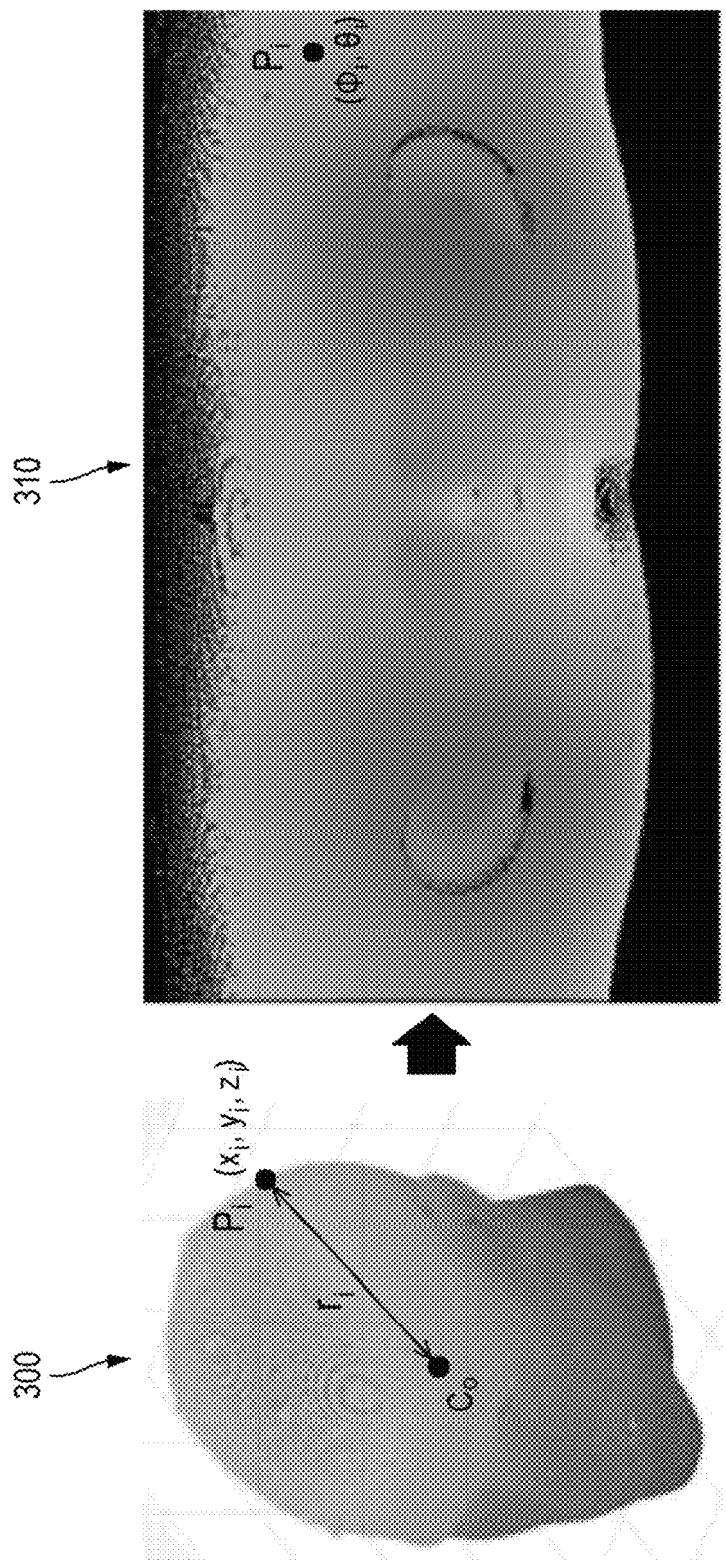
FIG. 3 illustrates model surface two-dimensional data, which have been converted two-dimensionally from model surface data, according to an embodiment of the present disclosure.

FIG. 3 illustrates model surface two-dimensional data 310, which have been converted two-dimensionally from model surface data 300, according to an embodiment of the present disclosure. The process of conversion from the model surface data 300 into the model surface two-dimensional data 310 may be performed by the first conversion unit 224 of FIG. 2.

As illustrated in FIG. 3, the model surface data 300 indicates the surface of the head of a person. According to an embodiment, the model surface data 300 may be generated by extracting surface data from model data (for example, CT/MRI data 10) generated by modeling the head of a person. Each point $P_i$ of the model surface data 300 has x-axis, y-axis, and z-axis coordinate values $(x_i, y_i, z_i)$.

The first conversion unit 224 calculates an average value of all points of the model surface data (300), thereby determining the center coordinate Co. The first conversion unit 224 parallel-moves the model surface data 300 such that the center coordinate Co becomes the origin (0,0,0) of the coordinate system. The first conversion unit 224 converts the xyz coordinate system (for example, $x_1y_1z_1$ coordinate system) into a $\phi\theta$ coordinate system (for example, $\phi_1\theta_1$ coordinate system) using equation 1 described with reference to FIG. 2, thereby generating model surface two-dimensional data 310, which is two-dimensional data, from the model surface data 300, which is three-dimensional data. The width coordinate of the model surface two-dimensional data 310 is $\phi$, and the height coordinate thereof is $\theta$. As illustrated in FIG. 3, a specific point $Pi(x_i, y_i, z_i)$ of the model surface data 300 corresponds to a specific point $Pi(\phi_i, \theta_i)$ of the model surface two-dimensional data 310.

In connection with the model surface data 300, $r_i$ refers to the distance from the center coordinate to a specific point $P_i$. In connection with the model surface two-dimensional data 310, $r_i$ at a specific point $P_i$ of the model surface data 300 refers to the brightness value of the corresponding point $P_i$. For example, in connection with the model surface data 300, points near the nose, chin, ears, forehead, and the back of the head, which have relatively large distances from the center coordinate, have data with large brightness values, when converted two-dimensionally. Furthermore, in connection with the model surface data 300, points near the eyes and cheeks, which have relatively small distances from the center coordinate, have data with small brightness values, when converted two-dimensionally.

Figure 4:
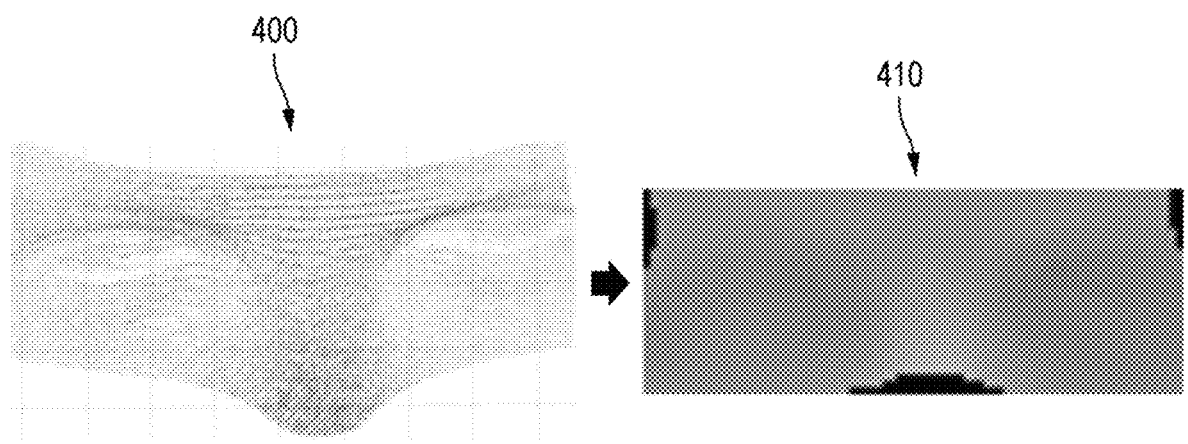
FIG. 4 and FIG. 5 illustrate measured surface two-dimensional data, which have been converted two-dimensionally from measured surface data, according to an embodiment of the present disclosure.
Figure 5:
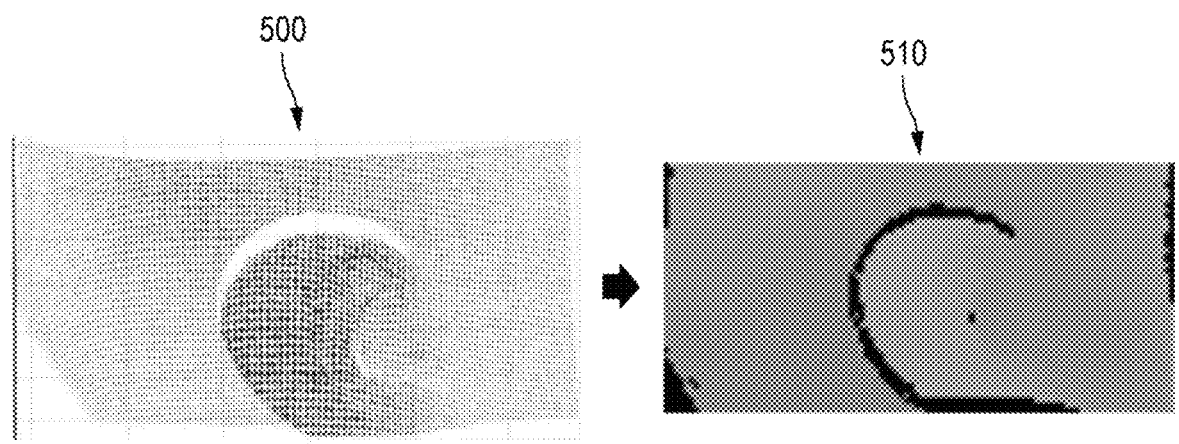

FIG. 4 illustrates measured surface two-dimensional data 410, which have been converted two-dimensionally from measured surface data 400, according to an embodiment of the present disclosure. In addition, FIG. 5 illustrates measured surface two-dimensional data 510, which have been converted two-dimensionally from measured surface data 500, according to an embodiment of the present disclosure. The process of conversion from the measured surface data 400 and 500 into the measured surface two-dimensional data 410 and 510 may be performed by the second conversion unit 226 of FIG. 2.

As illustrated in FIG. 4, the measured surface data 400 indicate the surface of the eyes and nose of a person, and the measured surface data 500 indicate the surface of ears of a person. According to an embodiment, the measured surface data 400 and 500 may be generated through scanning by the three-dimensional scanner 140 of FIG. 1. Each point of the measured surface data 400 and 500 has x-axis, y-axis, and z-axis coordinate values.

The second conversion unit 226 spherically unwraps the measured surface data 400 and 500, thereby generating measured surface two-dimensional data 410 and 510, respectively. When performing three-dimensional registration between the model surface data 300 of FIG. 3 and the measured surface data 400 and 500 of FIG. 4, the second conversion unit 226 may use the same type of conversion (for example, spherical unwrapping) as that of the two-dimensional conversion used by the first conversion unit 224 with regard to the model surface data 300.

The second conversion unit 226 generates a virtual sphere having the reference distance used for the two-dimensional conversion of the model surface data 300 as a radius. The second conversion unit 226 parallel-moves or rotation-moves each of the measured surface data 400 and 500 such that each of the measured surface data 400 and 500 is positioned on the surface of the virtual sphere. Thereafter, the second conversion unit 226 converts the xyz coordinate (for example, $x_2y_2z_2$ coordinate system) into a $\phi\theta$ coordinate system (for example, $\phi_1\theta_1$ coordinate system) using equation 1 described with reference to FIG. 2, based on the reference distance (for example, the radius of the virtual sphere). Consequently, measured surface two-dimensional data 410 and 510, which is two-dimensional data, is generated from the measured surface data 400 and 500, which is three-dimensional data. The width coordinate of the measured surface two-dimensional data 410 and 510 is $\phi$, and the height coordinate thereof is $\theta$.

Figure 6:
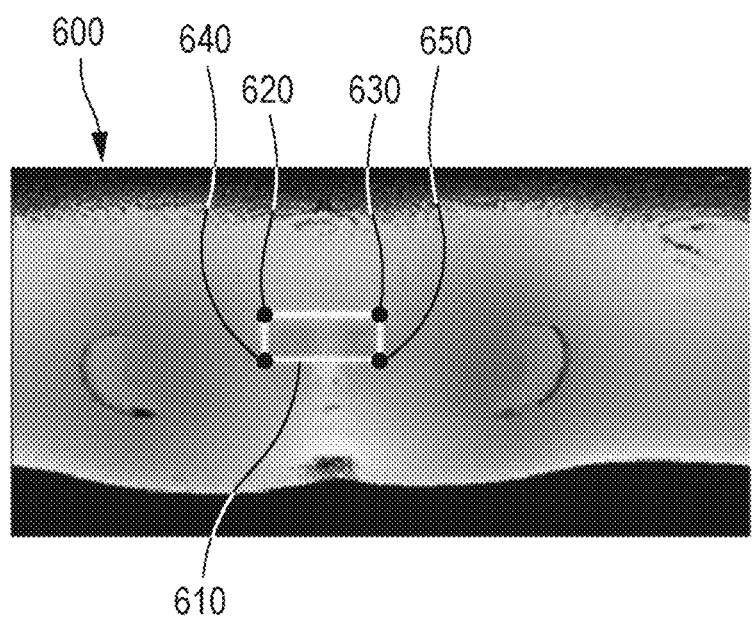
FIG. 6 and FIG. 7 illustrate measured surface two-dimensional data, which have been matched with model surface two-dimensional data, according to an embodiment of the present disclosure.
Figure 7:
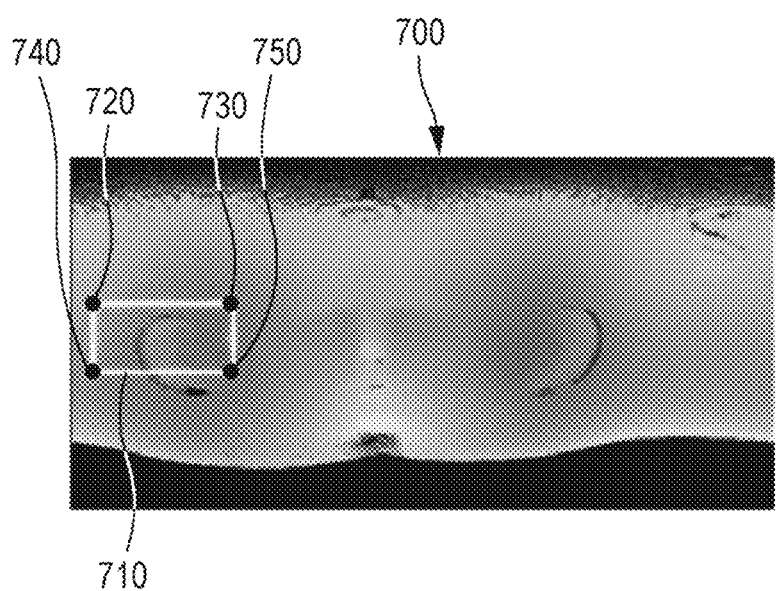

FIG. 6 illustrates measured surface two-dimensional data 610, which have been matched to model surface two-dimensional data 600, according to an embodiment of the present disclosure. In addition, FIG. 7 illustrates measured surface two-dimensional data 710, which have been matched to model surface two-dimensional data 700, according to an embodiment of the present disclosure. The model surface two-dimensional data 600 and 700 may be the model surface two-dimensional data 310 of FIG. 3. In addition, the measured surface two-dimensional data 610 may be at least a part of the measured surface two-dimensional data 410 of FIG. 4, and the measured surface two-dimensional data 710 may be at least a part of the measured surface two-dimensional data 510 of FIG. 5. The matching process in FIG. 6 and FIG. 7 may be performed by the initial position setting unit 228 of FIG. 2.

Referring to FIG. 6, the initial position setting unit 228 calculates the similarity of the measured surface two-dimensional data 610 with regard to the model surface two-dimensional data 600 while continuously parallel-moving the position of the measured surface two-dimensional data 610 by a predetermined distance or rotating the position of the measured surface two-dimensional data 610 by a predetermined angle. The initial position setting unit 228 may match the model surface two-dimensional data 600 and the measured surface two-dimensional data 610 by determining the position of the model surface two-dimensional data 600, which has the maximum similarity. In addition, the initial position setting unit 228 may determine points 620, 630, 640 and 650 that correspond to four vertices for defining matching areas between the model surface two-dimensional data 600 and the measured surface two-dimensional data 610. Similarly, the initial position setting unit 228 may match the model surface two-dimensional data 700 and the measured surface two-dimensional data 710 as illustrated in FIG. 7, and may determine points 720, 730, 740, and 750 that correspond to four vertices for defining matching areas.

As such, according to at least one embodiment of the present disclosure, in order to designate the initial position to be used for registration of three-dimensional data, it is possible to perform matching between two-dimensional data, which have been converted from three-dimensional data, instead of performing direct matching between the three-dimensional data to be registered. According to embodiments of the present disclosure, two-dimensional data, which have been converted from three-dimensional data, may be processed such that newly generated two-dimensional data may be matched to each other.

In addition, the matching areas are again converted three-dimensionally so as to set the initial position for registration in the three-dimensional data. Consequently, it is possible to set an appropriate initial position, thereby advantageously improving the accuracy and efficiency of registration between the three-dimensional data.

Figure 8:
FIG. 8 to FIG. 10 illustrate measured surface two-dimensional curvature data generated by partially differentiating model surface two-dimensional curvature data according to an embodiment of the present disclosure.
Figure 9:
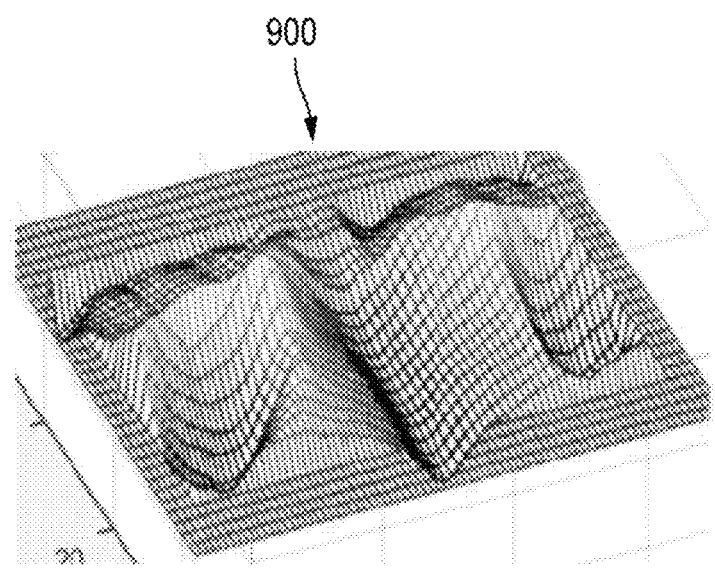
Figure 10:
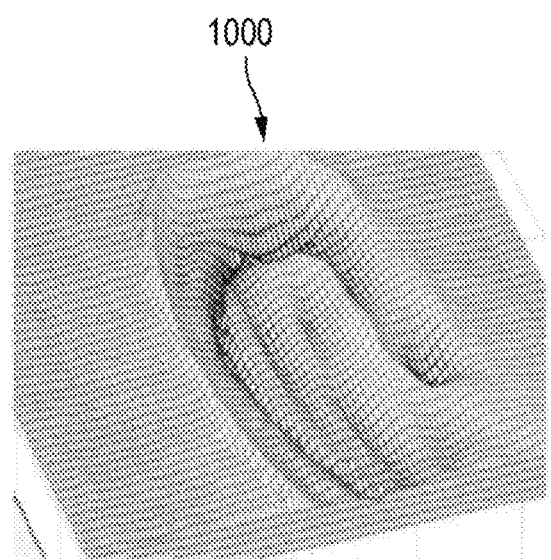

FIG. 8 illustrates model surface two-dimensional curvature data 800 generated by partially differentiating the model surface two-dimensional data 310 of FIG. 3 according to an embodiment of the present disclosure. In addition, FIG. 9 illustrates measured surface two-dimensional curvature data 900 generated by partially differentiating the measured surface two-dimensional data 410 of FIG. 4. In addition, FIG. 10 illustrates measured surface two-dimensional curvature data 1000 generated by partially differentiating the measured surface two-dimensional data 510 of FIG. 5. The curvature conversion process in FIG. 8 to FIG. 10 may be performed by the curvature conversion unit 230 of FIG. 2.

Referring to FIG. 8, in connection with the model surface two-dimensional curvature data 800, a point having a large difference from adjacent data (for example, points near contour lines of large ears, eyes, nose, and mouth) has a large curvature value. On the other hand, a point having a small difference from adjacent data (for example, points near cheeks or forehead) has a small curvature value. Referring to FIG. 9 and FIG. 10, in the case of the measured surface two-dimensional curvature data 900 and 1000, the greater the difference from the adjacent point is, the larger the curvature value is.

The model surface two-dimensional curvature data 800 illustrated in FIG. 8 exhibits a clearer change in data value than the model surface two-dimensional data 310 of FIG. 3. In addition, the measured surface two-dimensional curvature data 900 and 1000 illustrated in FIG. 9 and FIG. 10 exhibit a clearer change in data value than the measured surface two-dimensional data 410 and 510 of FIG. 4 and FIG. 5. As such, according to at least one embodiment of the present disclosure, in connection with matching two-dimensional data which have been converted from three-dimensional data, the curvature data, which are partially differentiated from the two-dimensional data are matched to each other. Consequently, the initial position is set more accurately, thereby advantageously further improving the accuracy and efficiency of registration between the three-dimensional data.

Figure 11:
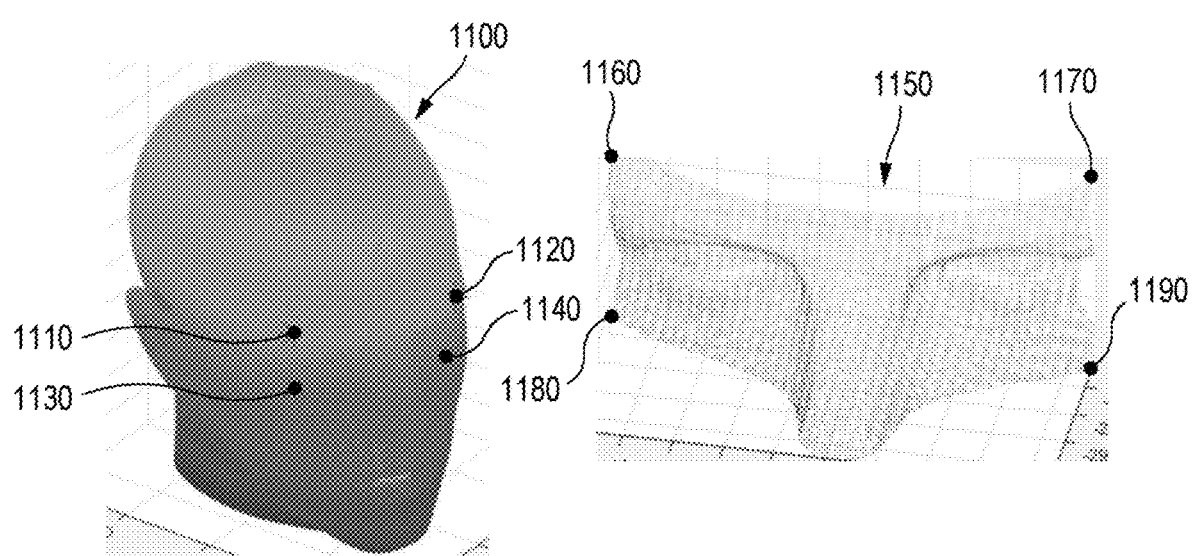
FIG. 11 and FIG. 12 illustrate model surface data and measured surface data with the initial positions set, according to an embodiment of the present disclosure.
Figure 12:
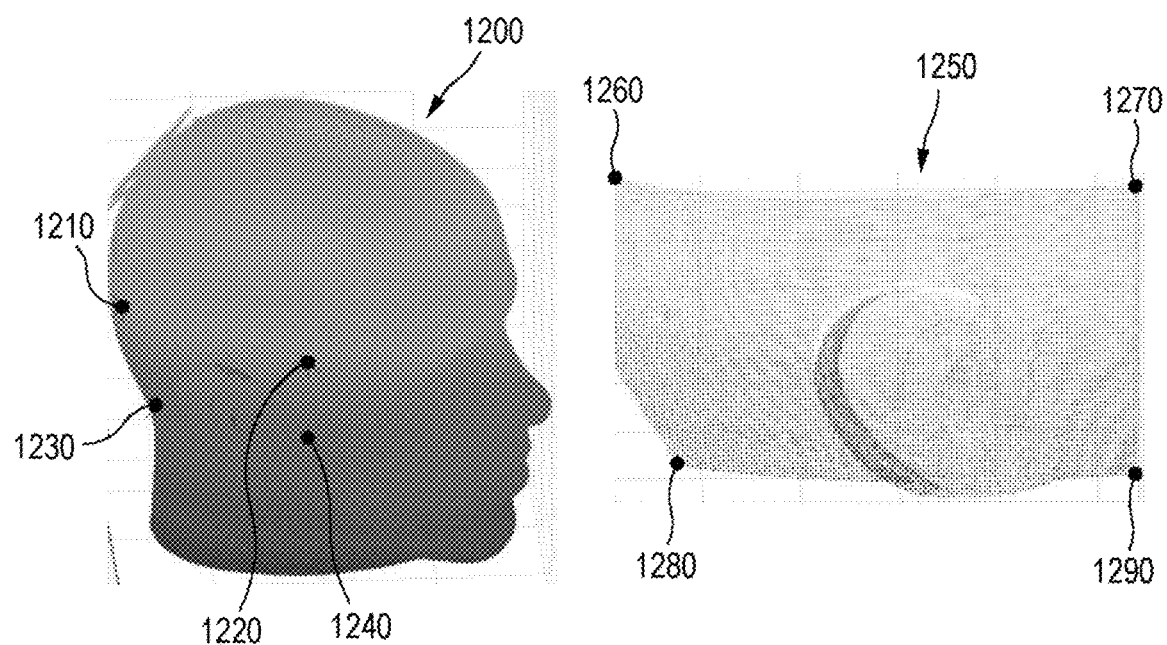

FIG. 11 illustrates model surface data 1100 and measured surface data 1150 with the initial positions set, according to an embodiment of the present disclosure. In addition, FIG. 12 illustrates model surface data 1200 and measured surface data 1250 with the initial positions set, according to an embodiment of the present disclosure. The initial position setting process in FIG. 11 and FIG. 12 may be performed by the initial position setting unit 228 of FIG. 2.

Referring to FIG. 11, the initial position setting unit 228 determines points 1110, 1120, 1130, and 1140 of the model surface data 1100, which correspond to the points 620, 630, 640, and 650 that are determined such that a matching area may be expressed in FIG. 6, and points 1160, 1170, 1180, and 1190 of the measured surface data 1150, which correspond to the points 620, 630, 640, and 650, as initial positions, respectively. The points 1110, 1120, 1130, and 1140 and the points 1160, 1170, 1180, and 1190 are obtained by converting the points 620, 630, 640, and 650, which have two-dimensional coordinate systems (for example, $\phi_1\theta_1$ coordinate system and $\phi_2\theta_2$ coordinate system), so as to have three-dimensional coordinate systems (for example, $x_1y_1z_1$ coordinate system and $x_1y_1z_1$ coordinate system) through inverse conversion of spherical unwrapping, respectively.

The points 1110, 1120, 1130, and 1140 and the points 1160, 1170, 1180, and 1190 are used as initial positions for registration between the model surface data 1100 and the measured surface data 1150, respectively. In other words, the model surface data 1100 and the measured surface data 1150 are registered three-dimensionally based on the points 1110, 1120, 1130, and 1140 and the points 1160, 1170, 1180, and 1190. For example, as a result of performing an ICP registration algorithm based on the points 1110, 1120, 1130, and 1140 and the points 1160, 1170, 1180, and 1190, the coordinate system (for example, $x_1y_1z_1$ coordinate system) of the model surface data 1100 is registered to have the coordinate system (for example, $x_2y_2z_2$ coordinate system) of the measured surface data 1150.

Referring to FIG. 12, the initial position setting unit 228 determines points 1210, 1220, 1230, and 1240 of the model surface data 1200, which correspond to the points 720, 730, 740, and 750 that are determined such that a matching area may be expressed in FIG. 7, and points 1260, 1270, 1280, and 1290 of the measured surface data 1250, which correspond to the points 720, 730, 740, and 750, respectively. The points 1210, 1220, 1230, and 1240 and the points 1260, 1270, 1280, and 1290 are obtained by converting the points 720, 730, 740, and 750, which have two-dimensional coordinate systems (for example, $\phi_1\theta_1$ coordinate system and $\phi_2\theta_2$ coordinate system), so as to have three-dimensional coordinate systems (for example, $x_1y_1z_1$ coordinate system and $x_1y_1z_1$ coordinate system) through inverse conversion of spherical unwrapping, respectively.

The points 1210, 1220, 1230, and 1240 and the points 1260, 1270, 1280, and 1290 are used as initial positions for registration between the model surface data 1200 and the measured surface data 1250, respectively. In other words, the model surface data 1200 and the measured surface data 1250 are registered three-dimensionally based on the points 1210, 1220, 1230, and 1240 and the points 1260, 1270, 1280, and 1290. For example, as a result of performing an ICP registration algorithm based on the points 1210, 1220, 1230, and 1240 and the points 1260, 1270, 1280, and 1290, the coordinate system (for example, $x_1y_1z_1$ coordinate system) of the model surface data 1200 is registered to have the coordinate system (for example, $x_2y_2z_2$ coordinate system) of the measured surface data 1250.

According to the present disclosure, the initial position is set accurately, thereby advantageously improving the accuracy and efficiency of registration between the three-dimensional data.

FIG. 13 is a flowchart of a method for registering three-dimensional data according to an embodiment of the present disclosure. At least some of the steps illustrated in FIG. 13 may be performed by the elements disclosed in FIG. 1 and FIG. 2.

Initially, in step S1300, model surface two-dimensional data is generated by two-dimensionally converting model surface data. For example, the first conversion unit 224 of FIG. 2 may average respective points of model surface data having a three-dimensional coordinate system, thereby determining the center coordinate, and may parallel-move the model surface data to the corresponding center coordinate. The first conversion unit 224 may spherically unwrap the model surface data to model surface two-dimensional data having a two-dimensional coordinate system by using the average value of distances from the center coordinate to each point of the model surface data as a reference distance.

The value (for example, brightness value) of each point of the model surface two-dimensional data may indicate the distance from a point of the model surface data, which corresponds to the corresponding point, to the center coordinate.

Next, in step S1310, measured surface two-dimensional data is generated by two-dimensionally converting measured surface data. For example, the second conversion unit 226 may generate a virtual sphere having the reference distance calculated in step S1300 as a radius. The second conversion unit 226 may move the measured surface data such that the measured surface data is positioned on the surface of the virtual sphere. Thereafter, the second conversion unit 226 may spherically unwrap the measured surface data to the measured surface two-dimensional data. The value (for example, brightness value) of each point of the measured surface two-dimensional data may indicate the distance from a point of the measured surface data, which corresponds to the corresponding point, to the center coordinate of the virtual sphere.

Next, in step S1320, the curvature of the model surface two-dimensional data and the curvature of the measured surface two-dimensional data are calculated. For example, the curvature conversion unit 230 may partially differentiate the model surface two-dimensional data generated in step S1300 and the measured surface two-dimensional data generated in step S1310, thereby generating model surface two-dimensional curvature data and measured surface two-dimensional curvature data. The value (for example, brightness value) of each point of the model surface two-dimensional curvature data may indicate the difference between the value of the corresponding point of the model surface two-dimensional data and the average value of a plurality of adjacent points. In addition, the value (for example, brightness value) of each point of the measured surface two-dimensional curvature data may indicate the difference between the value of the corresponding point of the surface measurement two-dimensional data and the average value of a plurality of adjacent points.

Next, in step S1330, a matching area is determined by matching the model surface two-dimensional curvature data and the measured surface two-dimensional curvature data. For example, based on the model surface two-dimensional curvature data and the measured surface two-dimensional curvature data generated in step S1320, the initial position setting unit 228 may determine an area of the model surface two-dimensional curvature data, which has maximum similarity to a predetermined area of the measured surface two-dimensional curvature data. The initial position setting unit 228 may determine a matching area within the determined area of the model surface two-dimensional curvature data. In addition, the initial position setting unit 228 may determine a matching area within a predetermined area of the measured surface two-dimensional curvature data, which is used for matching.

Next, in step S1340, initial positions are set with regard to the model surface data and the measured surface data, respectively. For example, the initial position setting unit 228 may set initial positions as a point of the model surface data, which corresponds to the matching area of the model surface two-dimensional curvature data determined in step S1330, and a point of the measured surface data, which corresponds to the matching area of the measured surface two-dimensional curvature data determined in step S1330, through inverse conversion of spherical unwrapping.

Next, in step S1350, the model surface data and the measured surface data are registered. For example, the data registration unit 232 may register the model surface data and the measured surface data by using the initial position of the model surface data and the initial position of the measured surface data, which are set in step S1340.

In addition, in connection with the steps illustrated in FIG. 13, some steps may be omitted, at least two steps may be performed simultaneously, or the order of performing the steps may be changed. According to an embodiment, step S1320 may be omitted and, in step S1330, the model surface two-dimensional data and the measured surface two-dimensional data may be matched so as to determine matching areas in the model surface two-dimensional data and the measured surface two-dimensional data, respectively. According to another embodiment, the method may further include, prior to step S1330, a step of receiving CT data or MRI data that indicates a three-dimensional model of the target, and a step of extracting surface data of the CT data or surface data of the MRI data from the corresponding CT data or MRI data as model surface data.

Although a method for registering three-dimensional data is described with reference to specific embodiments, it is also possible to implement the method as a computer-readable code in a computer-readable recording medium. The computer-readable recording medium includes every type of recording device in which computer-readable data is stored. Examples of the computer-readable recording medium include a ROM, a RAM, a CD-ROM, a magnetic tape, a floppy disk, and an optical data storage device, and also includes an instance of implementing the same as a carrier wave (for example, transmission through the Internet). In addition, the computer-readable recording medium may be distributed over computer systems connected through a network such that a computer-readable code can be stored and executed in a distributed manner. In addition, functional programs, codes, and code segments for implementing the above embodiments can be easily inferred by programmers in the technical field to which the present disclosure pertains.

Although the present disclosure is described and illustrated with reference to preferred embodiments, it would be understood by a person skilled in the art that various modifications and changes can be made without departing from the idea and scope of the claims.

We claim:

1. A method for registering three-dimensional data performed by a three-dimensional data registration device including a processor, comprising:
generating first two-dimensional data by two-dimensionally converting first three-dimensional data indicating a surface of a three-dimensional model of a target by the processor;
generating second two-dimensional data by two-dimensionally converting second three-dimensional data indicating at least a part of the surface of the three-dimensional model of the target by the processor;
determining a first matching area in the first two-dimensional data and a second matching area in the second two-dimensional data by matching the second two-dimensional data to the first two-dimensional data by the processor;
setting, as an initial position, a plurality of points of the first three-dimensional data, which correspond to the first matching area, and a plurality of points of the second three-dimensional data, which correspond to the second matching area by the processor; and registering the first three-dimensional data and the second three-dimensional data using the initial position by the processor, wherein the determining the first matching area and the second matching area comprises;

generating first two-dimensional curvature data and second two-dimenisonal curvature data by partially differentiating the first two-dimensional data and the second two-dimensional data, respectively; and determining the first matching area in the first two-dimensional curvature data and the second matching area in the second two-dimensional curvature data by matching the first two-dimensional curvature data and the second two-dimensional curvature data.

2. The method as claimed in claim 1, wherein the generating the first two-dimensional curvature data and the second two-dimensional curvature data comprises:

generating the first two-dimensional curvature data based on a value of each point in the first two-dimensional data and a value of a plurality of adjacent points; and generating the second two-dimensional curvature data based on a value of each point in the second two-dimensional data and a value of a plurality of adjacent points.

3. The method as claimed in claim 1, wherein the generating the first two-dimensional curvature data and the second two-dimensional curvature data comprises:

generating average curvature data indicating an average curvature of the first two-dimensional data or Gaussian curvature data indicating a Gaussian curvature of the first two-dimensional data as the first two-dimensional curvature data; and generating average curvature data indicating an average curvature of the second two-dimensional data or Gaussian curvature data indicating a Gaussian curvature of the second two-dimensional data as the second two-dimensional curvature data.

4. The method as claimed in claim 1, wherein the generating the first two-dimensional data by two-dimensionally converting the first three-dimensional data comprises:

determining a center coordinate of the first three-dimensional data;

calculating an average value of distances from the center coordinate to each point of the first three-dimensional data; and spherically unwrapping the first three-dimensional data to the first two-dimensional data using the calculated average value as a reference distance, wherein a value of each point of the first two-dimensional data indicates a distance from points of the first three-dimensional data, which correspond to each point of the first two-dimensional data, to the center coordinate.

5. The method as claimed in claim 4, wherein the generating the second two-dimensional data by two-dimensionally converting the second three-dimensional data comprises:

moving the second three-dimensional data such that the second three-dimensional data is positioned on a surface of a sphere having the reference distance as a radius; and spherically unwrapping the second three-dimensional data to the second two-dimensional data based on the reference distance, and wherein a value of each point of the second two-dimensional data indicates a distance from points of the second three-dimensional data, which correspond to each point of the second two-dimensional data, to a center coordinate of the sphere.

6. The method as claimed in claim 1, wherein the determining the first matching area and the second matching area comprises:

determining an area of the first two-dimensional data, which has maximum similarity to a predetermined area of the second two-dimensional data;

determining the first matching area within the determined area of the first two-dimensional data; and determining the second matching area within the predetermined area of the second two-dimensional data.

7. The method as claimed in claim 1, wherein the setting the initial position comprises setting the plurality of points of the first three-dimensional data, which correspond to the first matching area, and the plurality of points of the second three-dimensional data, which correspond to the second matching area, as the initial position.

8. The method as claimed in claim 1, further comprising:

receiving CT data or MRI data indicating the three-dimensional model of the target; and extracting surface data of the CT data or surface data of the MRI data from the CT data or the MRI data as the first three-dimensional data.

9. A device for registering three-dimensional data comprising:

a first conversion unit configured to generate first two-dimensional data by two-dimensionally converting first three-dimensional data indicating a surface of a three-dimensional model of a target;

a second conversion unit configured to generate second two-dimensional data by two-dimensionally converting second three-dimensional data indicating at least a part of the surface of the three-dimensional surface model of the target;

an initial position setting unit configured to determine a first matching area in the first two-dimensional data and a second matching area in the second two-dimensional data by matching the second two-dimensional data to the first two-dimensional data, and to set, as an initial position, a plurality of points of the first three-dimensional data, which correspond to the first matching area, and a plurality of points of the second three-dimensional data, which correspond to the second matching area;

a data registration unit configured to register the first three-dimensional data and the second three-dimensional data using the initial position; and a curvature conversion unit configured to generate first two-dimensional curvature data and second two-dimensional t Nature partially differentiating the first two-dimensional data and the second two-dimensional data, respectively, wherein the initial position setting unit is configured to determine the first matching area in the first two-dimensional curvature data and the second matching area in the second two-dimensional curvature data by matching the first two-dimensional curvature data and the second two-dimensional curvature data.

10. The device as claimed in claim 9, wherein the curvature conversion unit is configured to generate the first two-dimensional curvature data based on a value of each point in the first two-dimensional data and a value of a plurality of adjacent points, and to generate the second two-dimensional curvature data based on a value of each point in the second two-dimensional data and a value of a plurality of adjacent points.

11. The device as claimed in claim 9, wherein the curvature conversion unit is configured to generate average curvature data indicating an average curvature of the first two-dimensional data or Gaussian curvature data indicating a Gaussian curvature of the first two-dimensional data as the first two-dimensional curvature data, and to generate average curvature data indicating an average curvature of the second two-dimensional data or Gaussian curvature data indicating a Gaussian curvature of the second two-dimensional data as the second two-dimensional curvature data.

12. The device as claimed in claim 9, wherein the first conversion unit is configured to determine a center coordinate of the first three-dimensional data, to calculate an average value of distances from the center coordinate to each point of the first three-dimensional data, and to spherically unwrap the first three-dimensional data to the first two-dimensional data using the calculated average value as a reference distance, and wherein a value of each point of the first two-dimensional data indicates a distance from points of the first three-dimensional data, which correspond to each point of the first two-dimensional data, to the center coordinate.

13. The device as claimed in claim 12, wherein the second conversion unit is configured to move the second three-dimensional data such that the second three-dimensional data is positioned on a surface of a sphere having the reference distance as a radius, and to spherically unwrap the second three-dimensional data to the second two-dimensional data based on the reference distance, and wherein a value of each point of the second two-dimensional data indicates a distance from points of the second three-dimensional data, which correspond to each point of the second two-dimensional data, to a center coordinate of the sphere.

14. The device as claimed in claim 9, wherein the initial position setting unit is configured to determine an area of the first two-dimensional data, which has maximum similarity to a predetermined area of the second two-dimensional data, to determine the first matching area within the determined area of the first two-dimensional data, and to determine the second matching area within the predetermined area of the second two-dimensional data.

15. The device as claimed in claim 9, wherein the initial position setting unit is configured to set the plurality of points of the first three-dimensional data, which correspond to the first matching area, and the plurality of points of the second three-dimensional data, which correspond to the second matching area, as the initial position.

16. The device as claimed in claim 9, further comprising:

a communication unit configured to receive CT data or MRI data indicating the three-dimensional model of the target; and a surface extraction unit configured to extract surface data of the CT data or surface data of the MRI data from the CT data or the MRI data as the first three-dimensional data.

17. A non-transitory computer-readable recording medium storing a program comprising instructions for executing each step of a method for registering three-dimensional data, the method comprising: generating first two-dimensional data by two-dimensionally converting first three-dimensional data indicating a surface of a three-dimensional model of a target; generating second two-dimensional data by two-dimensionally converting second three-dimensional data indicating at least a part of the surface of the three-dimensional model of the target; determining a first matching area in the first two-dimensional data and a second matching area in the second two-dimensional data by matching the second two-dimensional data to the first two-dimensional data; setting, as an initial position, a plurality of points of the first three-dimensional data, which correspond to the first matching area, and a plurality of points of the second three-dimensional data, which correspond to the second matching area; and registering the first three-dimensional data and the second three-dimensional data using the initial position, wherein the determining the first matching area and the second matching area comprises:

generating first two-dimensional curvature data and second two-dimensional curvature data by partially differentiating the first two-dimensional data and the second two-dimensional data, respectively; and determining the first matching area in the first two-dimensional curvature data and the second matching area in the second two-dimensional curvature data by matching the first two-dimensional curvature data and the second two-dimensional curvature data.

\* \* \* \* \*